United States Patent
Zhu et al.

(10) Patent No.: US 10,858,479 B2
(45) Date of Patent: Dec. 8, 2020

(54) Y-TYPE DISCRETE POLYETHYLENE GLYCOL DERIVATIVE AND PREPARATION METHOD THEREOF

(71) Applicant: JenKem Technology Co., Ltd. (Beijing), Beijing (CN)

(72) Inventors: Hui Zhu, Beijing (CN); Meina Lin, Beijing (CN); Xuan Zhao, Beijing (CN)

(73) Assignee: JENKEM TECHNOLOGY CO., LTD. (BEIJING), Beijing (CN)

( * ) Notice: Subject to any disclaimer, the term of this patent is extended or adjusted under 35 U.S.C. 154(b) by 4 days.

(21) Appl. No.: 16/015,001

(22) Filed: Jun. 21, 2018

(65) Prior Publication Data

US 2018/0362712 A1 Dec. 20, 2018

Related U.S. Application Data (63) Continuation of application No. PCT/CN2016/109914, filed on Dec. 14, 2016.

(30) Foreign Application Priority Data

Dec. 21, 2015 (CN) .......................... 2015 1 0965247

(51) Int. Cl.
*C08G 65/48* (2006.01)
*C08G 65/332* (2006.01)
(Continued)

(52) U.S. Cl.
CPC ........... *C08G 65/48* (2013.01); *C08G 65/322* (2013.01); *C08G 65/325* (2013.01);
(Continued)

(58) Field of Classification Search
CPC .............. C08G 65/3322; C08G 65/322; C08G 65/325; C08G 65/3312; C08G 65/48;
(Continued)

(56) References Cited

U.S. PATENT DOCUMENTS 6,337,383 B1 * 1/2002 West ................... C08G 65/336
528/10
2002/0019491 A1 * 2/2002 Bruening ............. C07D 323/00
525/256

(Continued)

OTHER PUBLICATIONS

Allampally et al. (Chem. Eur. J. 2014, 20, 16863-16868).*
Kuo et al. (J.C.S. Chem. Comm., 1978).*
Allcock et al. (Macromolecules 1996,29, 1313-1319).*

*Primary Examiner* — Shane Fang
(74) *Attorney, Agent, or Firm* — Flener IP & Business Law; Zareefa B. Flener (57) ABSTRACT

The present invention relates to a Y-type discrete polyethylene glycol derivative as shown by Formula (I). The Y-type discrete polyethylene glycol derivative has the advantages of a determined molecular weight and number of segments in the chain, and can avoid the defects where the polyethylene glycol derivative itself is a mixture and the molecular weight is not homogeneous. The Y-type polyethylene glycol of the present invention can solve the problem of insufficient water solubility caused by an increase in the loading capacity when the discrete polyethylene glycol modifies an insoluble drug while increasing the drug loading capacity.

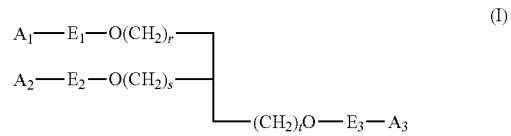

11 Claims, 4 Drawing Sheets

(51) Int. Cl.
    *C08G 65/322*     (2006.01)
    *C08G 65/325*     (2006.01)
    *C08G 65/331*     (2006.01)
    *A61K 47/10*     (2017.01)
    *C08K 5/053*     (2006.01)

(52) U.S. Cl.
    CPC ..... *C08G 65/3312* (2013.01); *C08G 65/3322* (2013.01); *A61K 47/10* (2013.01); *C08G 2650/42* (2013.01); *C08G 2650/50* (2013.01); *C08K 5/053* (2013.01)

(58) Field of Classification Search
    CPC ............ C08G 2650/42; C08G 2650/50; A61K 47/10; C08K 5/053
    See application file for complete search history.

(56) References Cited

U.S. PATENT DOCUMENTS

2011/0040113 A1*   2/2011   Wu ...................... C08G 65/329
                                                           554/227
2012/0232169 A1*   9/2012   Wu ...................... A61K 9/0014
                                                            514/786

* cited by examiner

Y-TYPE DISCRETE POLYETHYLENE GLYCOL DERIVATIVE AND PREPARATION METHOD THEREOF

CROSS-REFERENCE TO RELATED APPLICATION

This application is a continuation application of International patent application No. PCT/CN2016/109914, filed on Dec. 14, 2016, which claims the benefit and priority of Chinese patent application No. CN201510965247.1, filed on Dec. 21, 2015, each of which is incorporated herein by reference in its entirety and for all purposes.

FIELD OF THE INVENTION

The present invention relates to a Y-type discrete polyethylene glycol derivative and a preparation method thereof.

BACKGROUND OF THE INVENTION

As polyethylene glycol has good water solubility and biocompatibility, and no immunogenicity, polyethylene glycol (PEG) modification technology, also known as PEGylation, is often used as a method to increase the water solubility of poorly soluble drugs. It has been reported that the PEG-camptothecin with 20-hydroxyl group modified by $PEG_{40k}$ has solubility in water of about 2 mg/mL, which is 800 times the solubility of the original drug camptothecin (0.0025 mg/mL). Both the lactone group and the tertiary alcohol group at the 20 position in the structure of camptothecin are the basic active sites for inhibition of topoisomerase, the modification of 20-hydroxyl group by PEG improves the water solubility of the drug, and also improves the stability of the lactone group and gives the drug an antitumor targeting. Animal experiments showed that the concentration of the prodrug at the tumor site is 30 times that of camptothecin, which greatly improves its efficacy. At present, the drug has entered the clinical stage. In addition to camptothecin, modification of paclitaxel, scutellarin and other drugs by PEG can also greatly improve their water solubility and of oil-water distribution, thereby increasing the efficacy. PEG-modified paclitaxel, doxorubicin and cytarabine and other prodrugs have also entered the clinical trials stage.

However, as a chemically synthesized polymer, PEG itself is a mixture consisting of compounds with the same unit and different chain lengths. The molecular weight distribution index (Mw/Mn) thereof directly affects the relative molecular weight distribution of the modified drug, which in turn affects the homogeneity of the final product. The nature of multi-component mixing of PEG makes its derivatives bring about additional problems in impurity analysis, product testing, and results description, etc., which may even affect the efficacy and cause unwanted side reactions.

In order to ensure the homology of PEG-modified drugs, it is necessary to overcome the problem that polyethylene glycol is a mixture, Dhawan et al. (Synthesis of polyamide oligomers based on 14-amino-3,6,9,12-tetraoxatetradecanoic acid, Dhawan et al., Bioconjugate Chemistry 2000, 11, 14-21) prepared a linear discrete polyethylene glycol, which is similar in properties to PEG but is essentially a compound with a defined molecular weight that avoids the disadvantages of PEG as a mixture during drug modification, and even some of its properties are superior to those of PEG with the same chain segment.

Although the linear discrete polyethylene glycol solves the problem of non-uniformity of the final product due to PEG as a mixture during drug modification, it itself brings about new problems. Due to the limitation of the existing synthesis methods and purification methods, the obtained linear discrete polyethylene glycol has relatively small molecular weight and a larger loading than that of PEG when used for modification of drugs, but as a result, the modified poorly soluble drug has little improvement in water solubility compared with the original drug, which limits its application.

In order to overcome the drawbacks in the prior art, the present invention provides a Y-type discrete polyethylene glycol derivative and a preparation method thereof.

SUMMARY OF THE INVENTION

It is an object of the present invention to provide a Y-type discrete polyethylene glycol compound, which can overcome the drawback of non-uniformity of products of the existing polyethylene glycol-modified drugs, and which at the same time, as a discrete polyethylene glycol derivative having a branched structure, has more reactive sites and may increase loading for drugs than a linear polyethylene glycol.

It is another object of the present invention to solve the problem of insufficient water solubility of an interesting modified drug due to the increase of the loading when the discrete polyethylene glycol modifies the insoluble drugs.

Thus, one aspect of the present invention provides a Y-type discrete polyethylene glycol derivative having the structure of Formula (I):

wherein:

$A_1$, $A_2$, and $A_3$ are the same or different Y—X—$(CH_2)_n$ structures, wherein n is an integer from 0 to 12;

X is a linking group selected from the group consisting of —$(CH_2)_i$—, —$(CH_2)_i$NH—, —$(CH_2)_i$OCOO—, —$(CH_2)_i$OCONH—, —$(CH_2)_i$NHCONH—, —OC$(CH_2)_i$COO—, —$(CH_2)_i$COO— and —$(CH_2)_i$CONH—, i is an integer from 0 to 10;

Y is a reactive end group selected from the group consisting of hydrogen, $C_1$-$C_6$ alkyl, $C_1$-$C_6$ alkoxy, hydroxy (—OH), amino (—$NH_2$), aminomethyl (—$CH_2NH_2$), maleimido carboxyl (—COOH), sulfydryl (—SH), succinimide carbonate succinimide acetate (structure shown), succinimide propionate (structure shown), succinimide succinate (structure shown), succinimide (structure shown), dithiopyridinyl (4-pyridinedithiol, structure shown), propionic acid group (—CH₂CH₂COOH), aldehyde group (—CHO), thioester group $$(-\overset{O}{\underset{\|}{C}}-S-),$$

acryloxy $$(-O-\overset{O}{\underset{\|}{C}}-CH=CH_2),$$

azido (—N₃), glutaric acid group (—OCOCH₂CH₂CH₂COOH), hydrazide (—CONHNH₂), alkynyl (—C≡CH), p-nitrophenyl carbonate (structure shown), isocyanato (—NCO), o-dithiopyridinyl (2-pyridinedithiol, (structure shown), silane (e.g., —Si(CH₃)₃, —Si(CH₂CH₃)₃, —Si(CH₂CH₂CH₃)₃), carboxymethyl (—CH₂COOH), vinyl sulfone group (structure shown)

and vitamin H (structure shown);

$E_1$ is a discrete polyethylene glycol group with a structure of $(CH_2CH_2O)_j$, j is an integer from 0 to 100;

$E_2$ is a discrete polyethylene glycol group with a structure of $(CH_2CH_2O)_k$, k is an integer from 0 to 100;

$E_3$ is a discrete polyethylene glycol group with a structure of $(CH_2CH_2O)_l$, l1 is an integer from 0 to 100;

and, r, s and t are independently selected from the group consisting of 0, 1, 2 or 3.

Preferably, in the structure of Formula (I) according to the present invention, the i in the linking group X is an integer from 0 to 6; more preferably, the i is 0, 1, 2, 3 or 4; the linking group X is preferably —(CH₂)ᵢ—, —(CH₂)ᵢNH— or —(CH₂)ᵢCONH—.

Preferably, in the structure of Formula (I) according to the present invention, the reactive end group Y is selected from the group consisting of hydrogen, methyl, ethyl, methoxy (—OCH$_3$), ethoxy (—OCH$_2$CH$_3$), hydroxy, amino, sulfydryl, carboxyl, ester group, aldehyde group, acryloxy, maleimide, vinyl sulfone group and vitamin H, etc.

Preferably, in the structure of Formula (I), the j in the discrete polyethylene glycol group E$_1$ is an integer from 0 to 20; more preferably, the j is an integer from 1 to 12; and most preferably the j is 1, 2, 3, 4, 5, 6, 7 or 8.

Preferably, in the structure of Formula (I), the k in the discrete polyethylene glycol group E$_2$ is an integer from 0 to 20; more preferably, the k is an integer from 1 to 12; and most preferably the k is 1, 2, 3, 4, 5, 6, 7 or 8.

Preferably, in the structure of Formula (I), the l in the discrete polyethylene glycol group E$_3$ is an integer from 0 to 20; more preferably, the l is an integer from 1 to 12; and most preferably the l is 1, 2, 3, 4, 5, 6, 7 or 8.

In the structure of Formula (I) of the present invention, preferably, at least two of the j, k, and l in the discrete polyethylene glycol groups are the same and are not zero.

In the structure of Formula (I) of the present invention, the r, s and t may be independently selected from 0, 1, 2 or 3, for example, the r, s and t are all 0; the r is 0, the s is 0, the t is 2; the r is 0, the s is 0, the t is 3; the r is 1, the s is 1, the t is 2; or, the r, s and t are all 2; etc.

Preferably, in an embodiment of the present invention, the r, s, and t are all 0, the Y-type discrete polyethylene glycol derivative is a Y-type discrete polyethylene glycol derivative with glycerol as a core and having a structure of Formula (II):

$$A_1-E_1-O-\!\!\begin{array}{l}\\ \\ \end{array}\quad (II)$$
$$A_2-E_2-O-\!\!\begin{array}{l}\\ \\ \end{array}$$
$$\qquad\qquad O-E_3-A_3.$$

In an embodiment of the present invention, the Y-type discrete polyethylene glycol derivative has a structure of Formula (III):

$$A_1-E_1-O(CH_2)_r-\!\!\begin{array}{l}\\ \\ \end{array}\quad (III)$$
$$A_2-E_2-O(CH_2)_s-\!\!\begin{array}{l}\\ \\ \end{array}$$
$$\qquad\qquad (CH_2)_t-O-A_3;$$

the r, s, and t are independently selected from 0, 1, 2, or 3; preferably, the r, s, and t are all 0.

In an embodiment of the present invention, the Y-type discrete polyethylene glycol derivative has a structure of Formula (IV):

$$CH_3-E_1-O(CH_2)_r-\!\!\begin{array}{l}\\ \\ \end{array}\quad (IV)$$
$$CH_3-E_2-O(CH_2)_s-\!\!\begin{array}{l}\\ \\ \end{array}$$
$$\qquad\qquad OH;$$

the r and s are independently selected from 0, 1, 2, or 3; preferably, both r and s are 0.

In an embodiment of the present invention, the Y-type discrete polyethylene glycol derivative has a structure of Formula (V):

$$H-E_1-O(CH_2)_r-\!\!\begin{array}{l}\\ \\ \end{array}\quad (V)$$
$$H-E_2-O(CH_2)_s-\!\!\begin{array}{l}\\ \\ \end{array}$$
$$\qquad\qquad OH;$$

the r and s are independently selected from 0, 1, 2, or 3; preferably, both r and s are 0.

In an embodiment of the present invention, the Y-type discrete polyethylene glycol derivative has a structure of Formula (VI):

$$NH_2CH_2CH_2-E_1-O(CH_2)_r-\!\!\begin{array}{l}\\ \\ \end{array}\quad (VI)$$
$$NH_2CH_2CH_2-E_2-O(CH_2)_s-\!\!\begin{array}{l}\\ \\ \end{array}$$
$$\qquad\qquad OH;$$

the r and s are independently selected from 0, 1, 2, or 3; preferably, both r and s are 0.

In an embodiment of the present invention, the Y-type discrete polyethylene glycol derivative has a structure of Formula (VII):

$$HOOCCH_2CH_2-E_1-O(CH_2)_r-\!\!\begin{array}{l}\\ \\ \end{array}\quad (VII)$$
$$HOOCCH_2CH_2-E_2-O(CH_2)_s-\!\!\begin{array}{l}\\ \\ \end{array}$$
$$\qquad\qquad OH;$$

the r and s are independently selected from 0, 1, 2, or 3; preferably, both r and s are 0.

In an embodiment of the present invention, the Y-type discrete polyethylene glycol derivative has a structure of Formula (VIII):

$$CH_3-E_1-O(CH_2)_r-\!\!\begin{array}{l}\\ \\ \end{array}\quad (VIII)$$
$$CH_3-E_2-O(CH_2)_s-\!\!\begin{array}{l}\\ \\ \end{array}$$
$$\qquad\qquad (CH_2)_t-O-E_3-A_3;$$

the r, s, and t are independently selected from 0, 1, 2, or 3; preferably, the r, s, and t are all 0.

In an embodiment of the present invention, the Y-type discrete polyethylene glycol derivative has a structure of Formula (IX):

$$CH_3-E_1-O(CH_2)_r-\!\!\begin{array}{l}\\ \\ \end{array}\quad (IX)$$
$$CH_3-E_2-O(CH_2)_s-\!\!\begin{array}{l}\\ \\ \end{array}$$
$$\qquad\qquad (CH_2)_t-O-E_3-H;$$

the r, s, and t are independently selected from 0, 1, 2, or 3; preferably, the r, s, and t are all 0.

Another aspect of the present invention provides a preparation method of the Y-type discrete polyethylene glycol derivative having the structure of Formula (I), the steps of which include:

(1) halogenating or sulfonating one or more end-group-modified discrete polyethylene glycol derivatives; (2) reacting any of the products obtained in step (1) with at least one hydroxyl group of a core compound; and, (3) optionally, modifying the end group(s) of the product of step (2) to give a Y-type discrete polyethylene glycol derivative having the structure of Formula (I), or, modifying the end group(s) of the product of step (2) into a hydroxyl group, then reacting with any of the products obtained in step (1), modifying the end group(s) of the obtained product to give a Y-type discrete polyethylene glycol derivative having the structure of Formula (I).

In the step (1) of the preparation method of the Y-type discrete polyethylene glycol derivative of the present invention, the end-group-modified discrete polyethylene glycol derivative has a structure of Z—X—$(CH_2)_n$-E-OH, wherein:
X is a linking group selected from the group consisting of —$(CH_2)_i$—, —$(CH_2)_i$NH—, —$(CH_2)_i$OCOO—, —$(CH_2)_i$OCONH—, —$(CH_2)_i$NHCONH—, —OC$(CH_2)_i$COO—, —$(CH_2)_i$COO— and —$(CH_2)_i$CONH—, i is an integer from 0 to 10;

Z is selected from the group consisting of the active end groups defined by the Y in the structure of Formula (I) according to the present invention, or, Z is selected from the group consisting of methyl ester group (—COOCH$_3$), ethyl ester group (—COOCH$_2$CH$_3$), tert-butyl ester group (—COOC(CH$_3$)$_3$), aldehyde acetal group (e.g., benzyloxy tert-butoxy imidogen (—NHCH$_3$), halogen and hydroxy;

the Y is: hydrogen, $C_1$-$C_6$ alkyl, $C_1$-$C_6$ alkoxy, hydroxy, amino, aminomethyl, maleimido, carboxyl, sulfydryl, succinimide carbonate, succinimide acetate, succinimide propionate, succinimide succinate, succinimide, dithiopyridinyl, propionic acid group, aldehyde group, thioester group, acryloxy, azido, glutaric acid group, hydrazide, alkynyl, p-nitrophenyl carbonate, isocyanato, o-dithiopyridinyl, silane, carboxymethyl, vinyl sulfone group or vitamin H; preferably, Y is selected from the group consisting of H, methyl, ethyl, methoxy, ethoxy, hydroxy, amino, sulfydryl, carboxyl, ester group, aldehyde group, acryloxy, maleimide, vinyl sulfone group and vitamin H.

Preferably, the Z is methyl ester group, ethyl ester group, tert-butyl ester group, azido, aldehyde acetal group or benzyloxy.

E is a discrete polyethylene glycol group with a structure of $(CH_2CH_2O)_a$, a is an integer from 0 to 100; preferably a is an integer from 0 to 20; more preferably a is an integer from 0 to 12; most preferably a is 1, 2, 3, 4, 5, 6, 7 or 8.

In the step (2) of the preparation method of the Y-type discrete polyethylene glycol derivative of the present invention, the core compound has a structure represented by the following formula (X):

wherein:
r, s, and t are independently selected from 0, 1, 2, 3; r, s, and t are preferably 0;

$R_1$, $R_2$ and $R_3$ are selected from the group consisting of hydroxy, allyloxy, benzyloxy, tert-butoxy, azido, imino, ester, halogen, methoxy, ethoxy, amino, sulfydryl, carboxyl, aldehyde group, acryloxy, maleimide, vinyl sulfone group and vitamin H; more preferably, $R_1$, $R_2$ and $R_3$ are selected from the group consisting of hydroxy, allyloxy, benzyloxy, tert-butoxy, azido, imino, ester and halogen; and at least one of $R_1$, $R_2$ and $R_3$ is hydroxy.

In a specific embodiment of the present invention, preferably, two of $R_1$, $R_2$ and $R_3$ in the core compound are hydroxy.

In a specific embodiment of the present invention, the step (1) may be: adding methylene chloride (DCM) in a volume ratio of 1 to 100 times, preferably 1 to 20 times, more preferably 1 to 10 times, and triethylamine (TEA) in a molar ratio of 1 to 5 times, preferably 1 to 3 times, to one end-group-modified discrete polyethylene glycol derivative (as the basis), then dissolving methane chloride (MsCl) or p-toluenesulfonyl chloride in a molar ratio of 1-3 times, preferably 1-2 times, in methylene chloride in a volume ratio of 1 to 30 times, preferably 1 to 20 times, more preferably 1 to 15 times, and adding dropwise into a reaction flask, reacting at room temperature for 1 to 48 hours, preferably for 2 to 16 hours, washing the reaction solution with water 1-3 times, drying the organic phase with anhydrous sodium sulfate, filtering to remove the sodium sulfate, evaporating the solvent to dryness and concentrating to give a product, i.e., the sulfonylated product of the end-group-modified discrete polyglycol derivative.

In a preferred embodiment of the present invention, the reaction for sulfonating the end-group-modified discrete polyethylene glycol derivative in the step (1) is as follows:

wherein, the G is methyl or p-tolyl.

In a specific embodiment of the present invention, the step (2) of the preparation method of the Y-type discrete polyethylene glycol derivative includes: adding toluene in a volume ratio of 1 to 50 times, preferably 10 to 40 times, more preferably 20 to 35 times, to the core compound (as the basis), adding 60% sodium hydride with a mass-to-volume ratio of 0.5-1.0 g/mL under an ice-water bath, reacting for 1 to 3 hours at room temperature, adding dropwise the product of step (1) in a mass ratio of 5-10 times to sodium hydride, and toluene in a volume ratio of 1 to 50 times, preferably 10 to 40 times, more preferably 20 to 35 times, reacting at 60-70° C. for 1 to 48 hours, preferably 6 to 18 hours, evaporating the toluene to dryness, adding dichloromethane and water, each washing once, evaporating the dichloromethane to dryness, and column-purifying (mobile phase being 1-3% methanol/dichloromethane) to give a product.

In a preferred embodiment of the present invention, the reaction in the step (2) of the preparation method of the Y-type discrete polyethylene glycol derivative is as follows:

linked to the core group through a one-step reaction; under the condition that the three discrete polyethylene glycol derivatives to be linked are different, the linkages can be performed one after the other, for example, firstly, one end-group-protected discrete polyethylene glycol derivative is synthesized and then reacted with the core group having two end groups protected; then the end groups of the core group is deprotected and further modified to obtain a desired discrete polyethylene glycol derivative.

In the step (3) of the preparation method of the present invention, the end group(s) can be modified according to the Y-type discrete polyethylene glycol derivative to be prepared. According to the application fields and methods of the Y-type discrete polyethylene glycol derivative, it is sometimes necessary to modify the Y-type derivative synthesized, that is, to modify the 1-3 end groups of the Y-type derivative into the desired reactive group. This modification can be carried out before the step (1): for example, first synthesizing a discrete polyethylene glycol derivative having one end wherein, W is —OMs, —OTs, —Cl, —Br, or —I, etc.;
$Z_1$ and $Z_2$ are selected from the group consisting of the reactive end groups defined by the Z, which are the same or different active end groups; and
$E_1$ and $E_2$ are selected from the group consisting of discrete polyethylene glycol groups defined by the E, which are the same or different discrete polyethylene glycol groups.

In a specific embodiment, in the preparation method according to the present invention, the same or different discrete polyethylene glycol derivatives can be linked on the core group as required. Under the condition that the three discrete polyethylene glycol derivatives to be linked to the core group are the same, one synthesized end-group-protected discrete polyethylene glycol derivative can be directly group as protected reactive group, mesylating, Y-forming, deprotecting, to obtain give a Y-type derivative having two end groups as reactive groups; or, first synthesizing a Y-type derivative, modifying the end group to give a Y-type derivative having one end groups as reactive group; or, further applying both of the above two methods to give a Y-type derivative having three modified end groups. There are many specific modification methods, which can be related synthetic methods that are easily available in the field, such as carboxylation and subsequent succinimidation, amination, aldehyde-forming, thiolation, maleimidation, acrylation, and the like.

The Y-type discrete polyethylene glycol derivative of the present invention has the advantages of uniform molecular weight and high drug loading, and the poorly soluble drug molecule modified with the Y-type discrete polyethylene glycol derivative of the present invention has significantly improved water solubility compared with the original drug molecule and drug molecule modified with the linear polyethylene glycol derivative.

DETAILED DESCRIPTION OF THE INVENTION

Example 1: Synthesis of $(mEG_3)_2$-OH (1)

Figure 1:
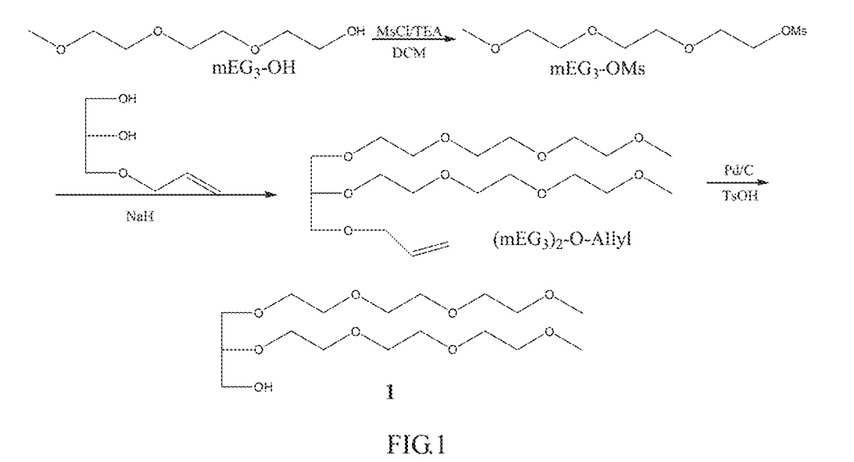
FIG. 1 is a synthetic route diagram of the Y-type discrete polyethylene glycol derivative $(mEG_3)_2$-OH (1).

The synthetic route is shown in FIG. 1.
1. Synthesis of $mEG_3$-OMs

TEA (32 mL, 230 mmol) and DCM (150 mL) were added to $mEG_3$-OH (32 mL, 200 mmol), the resulting mixture was placed in a reaction flask in an ice-water bath. MsCl (17.5 mL, 220 mmol) was dissolved with DCM (50 mL), and when dissolved completely, the resulting mixture was dropwise added into the reaction flask in ice-water bath. The reaction was performed at room temperature for 3 hours. The completeness of the reaction was checked by thin layer chromatography (TLC). The reaction mixture was washed three times with water (150 mL). The organic phase was dried over anhydrous sodium sulfate and then the sodium sulfate was removed by filtration. About 52 g product was obtained after concentration.

2. Synthesis of $(mEG_3)_2$-O-Allyl

Toluene (75 mL) was added to 3-allyloxy-1,2-propanediol (3.01 mL), NaH (60%, 2.05 g) was added under ice-water bath. The reaction was performed at room temperature for 2 hours. A solution of $mEG_3$-OMs (13 g) in toluene (80 mL) was added dropwise and the reaction was continued overnight at 60° C. The reaction mixture was detected by HPLC, the toluene was evaporated to dryness, the resulting mixture was washed once each with DCM and water, the DCM was evaporated to dryness to give a crude product. The crude product was purified with a column (mobile phase: 1% MeOH/DCM) to give a product (8.8 g, yield: 85%).

3. Synthesis of Y—Type Small Molecule 1

Pd/C (0.8 g) and TsOH (1.6 g) were added to the product of the previous step (8 g), and methanol (80 mL)/water (16 mL) was added, the resulting mixture was refluxed for 24 hours. Upon completion of the reaction detected by HPLC, the reaction mixture was filtered to recover Pd/C and concentrated to give a crude product. The crude product was purified with a column (3% MeOH/DCM) to give a product (5.8 g, yield: 80.2%).

NMR (CDCl$_3$) δ: 3.89-3.50 (m, 29H), 3.38 (s, 6H); ESI-MS: 385.4 (M+H)$^+$, 407.2 (M+Na)$^+$.

Example 2: Synthesis of $(mEG_5)_2$-OH (2)

Figure 2:
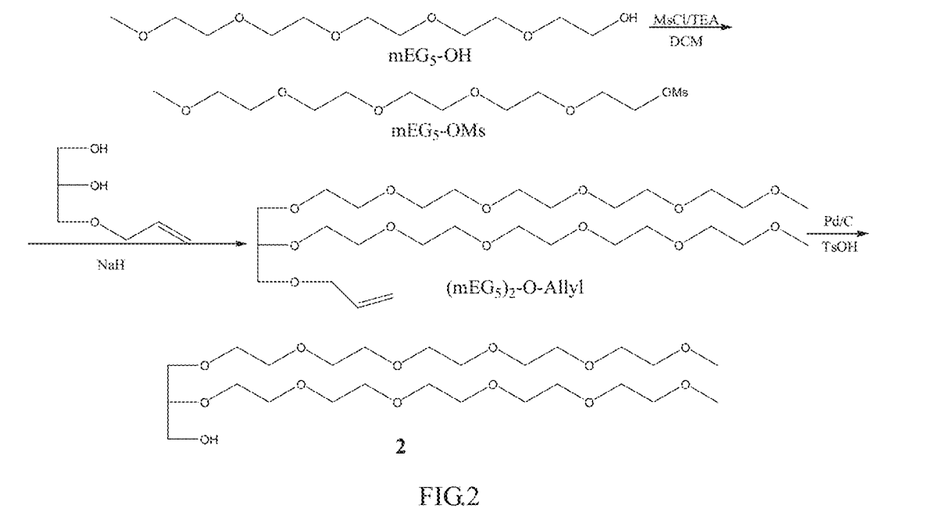
FIG. 2 is a synthetic route diagram of the Y-type discrete polyethylene glycol derivative $(mEG_5)_2$-OH (2).

The synthetic route is shown in FIG. 2.
1. Synthesis of $mEG_5$-OMs

TEA (6.86 mL) and DCM (60 mL) were added to $mEG_5$-OH (10.08 g), the resulting mixture was placed in a reaction flask in an ice-water bath. MsCl (3.56 mL) was dissolved with DCM (50 mL), the resulting mixture was dropwise added into the reaction flask in ice-water bath. The reaction was performed at room temperature for 3 hours. The completeness of the reaction was checked by TLC. The reaction mixture was washed three times with water. The organic phase was dried over anhydrous sodium sulfate and then the sodium sulfate was removed by filtration. About 9.8 g product was obtained after concentration.

2. Synthesis of $(mEG_5)_2$-O-Allyl

Toluene (40 mL) was added to 3-allyloxy-1,2-propanediol (1.22 mL), NaH (60%, 0.79 g) was added under ice-water bath. The reaction was performed at room temperature for 2 hours. A solution of $mEG_5$-OMs (6.9 g) in toluene (40 mL) was added dropwise and the reaction was continued overnight at 60° C. The reaction mixture was detected by HPLC, the toluene was evaporated to dryness, the resulting mixture was washed once each with DCM and water, the DCM was evaporated to dryness to give a crude product. The crude product was purified with a column (mobile phase: 1% MeOH/DCM) to give a product (4.7 g, yield: 83%).

3. Synthesis of Y-Type Small Molecule 2

Pd/C (0.4 g) and TsOH (0.8 g) were added to the product of the previous step (4 g), and methanol (40 mL)/water (8 mL) was added, the resulting mixture was refluxed for 24 hours. Upon completion of the reaction detected by HPLC, the reaction mixture was filtered to recover Pd/C and concentrated to give a crude product. The crude product was purified with a column (3% MeOH/DCM) to give a product (3.0 g, yield: 82%).

NMR (CDCl$_3$) δ: 3.89-3.50 (m, 45H), 3.38 (s, 6H); ESI-MS: 561.4 (M+H)$^+$.

Example 3: Synthesis of $(HO-EG_4)_2$-OH (3)

Figure 3:
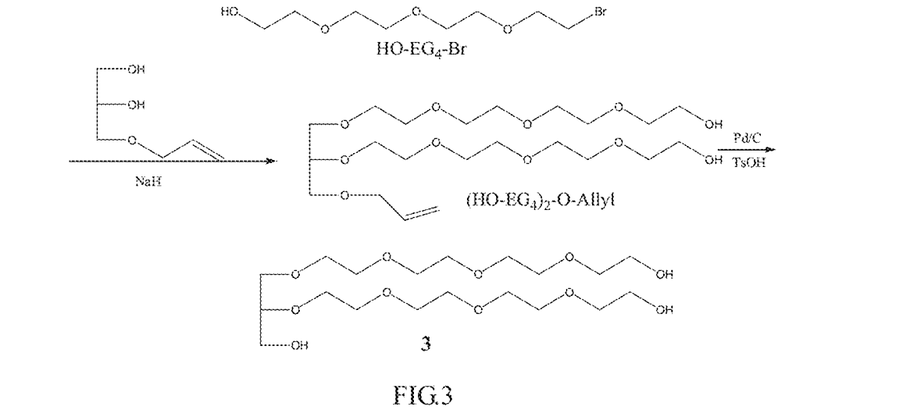
FIG. 3 is a synthetic route diagram of the Y-type discrete polyethylene glycol derivative $(HO-EG_4)_2$-OH (3).

The synthetic route is shown in FIG. 3.
1. Synthesis of $(HO-EG_4)_2$-O-Allyl

Toluene (75 mL) was added to 3-allyloxy-1,2-propanediol (2.43 mL), NaH (60%, 1.57 g) was added under ice-water bath. The reaction was performed at room temperature for 2 hours. A solution of $HO-EG_4$-Br (10.6 g) in toluene (80 mL) was added dropwise and the reaction was continued overnight at 70° C. The reaction mixture was detected by HPLC, the toluene was evaporated to dryness, the resulting mixture was washed once each with DCM and water, the DCM was evaporated to dryness to give a crude product. The crude product was purified with a column (mobile phase: 1% MeOH/DCM) to give a product (7.3 g, yield: 80%).

2. Synthesis of Y-Type Small Molecule 3

Pd/C (0.6 g) and TsOH (1.2 g) were added to the product of the previous step (6 g), and methanol (60 mL)/water (12 mL) was added, the resulting mixture was refluxed for 24 hours. Upon completion of the reaction detected by HPLC, the reaction mixture was filtered to recover Pd/C and concentrated to give a crude product. The crude product was purified with a column (3-4% MeOH/DCM) to give a product (4.3 g, yield: 78%).

NMR (CDC$_3$) δ: 3.89-3.50 (m, 36H), 3.25 (m, 1H); ESI-MS: 445.4 (M+H)$^+$, 467.4 (M+Na)$^+$.

Example 4: Synthesis of (NHrEG$_4$)$_2$-OH (4)

Figure 4:
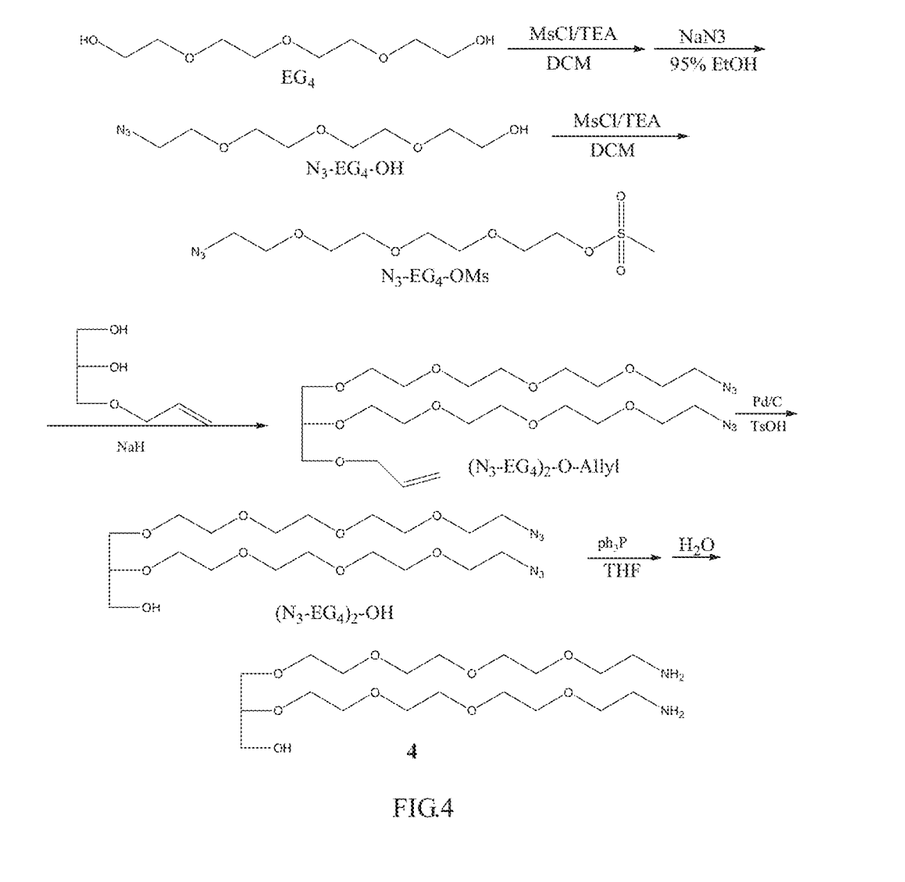
FIG. 4 is a synthetic route diagram of the Y-type discrete polyethylene glycol derivative $(NH_2-EG_4)_2$-OH (4).

The synthetic route is shown in FIG. 4.

1. Synthesis of N$_3$-EG$_4$-OH

EG$_4$ (36 mL, 210 mmol), DCM (100 mL) and TEA (25 mL) were added to a reaction flask which was placed in an ice-water bath. A solution of MsCl (5.81 mL, 75 mmol) in DCM (100 mL) was added dropwise. The reaction was performed at room temperature for 4 hours. The reaction mixture was washed once with water (100 mL) and evaporated to dryness to give a crude product.

To the crude product of the previous step, 95% ethanol (150 mL) and sodium azide (6.5 g, 100 mmol) were added, and the resulting mixture was refluxed at room temperature for 16 hours. The reaction mixture was filtered to remove solids and the resulting solution was evaporated to dryness. The resulting solid was added with DCM (150 mL) and washed three times with water (100 mL). The DCM phase was evaporated to dryness to give a crude product. The crude product was purified with a column (mobile phase: PE/EA=50-0%) to give a product (13.1 g, yield: 28.4%).

2. Synthesis of N$_3$-EG$_4$-OMs

To the N$_3$-EG$_4$-OH prepared in above Step 1 (11 g, 50.2 mmol), TEA (8.6 mL, 60.3 mmol) and DCM (150 mL) were added and placed in an ice-water bath. MsCl (4.5 mL, 57.8 mmol) was dissolved in DCM (50 mL) and added dropwise to the reaction flask in ice-water bath. The reaction was performed at room temperature overnight. The completeness of the reaction was checked by TLC. The reaction mixture was washed three times with water (100 mL). The organic phase was dried over anhydrous sodium sulfate and then the sodium sulfate was removed by filtration. About 14.2 g product (yield: 95%) was obtained after concentration.

3. Synthesis of (N$_3$-EG$_4$)$_2$-O-Allyl

Toluene (40 mL) was added to 3-allyloxy-1,2-propanediol (1.22 mL), NaH (60%, 0.79 g) was added under an ice-water bath. The reaction was performed at room temperature for 2 hours. A solution of N$_3$-EG$_4$-OMs (6.1 g) in toluene (80 mL) was added dropwise and the reaction was continued overnight at 60° C. The reaction mixture was detected by HPLC, the toluene was evaporated to dryness, the resulting mixture was washed once each with DCM and water, the DCM was evaporated to dryness to give a crude product. The crude product was purified with a column (mobile phase: 1% MeOH/DCM) to give a product (4.3 g, yield: 85%).

4. Synthesis of (N$_3$-EG$_4$)$_2$-OH

To the product (4 g) of the previous step, Pd/C (0.4 g), TsOH (0.8 g) were added, methanol (40 mL)/water (8 mL) was added, the resulting mixture was refluxed for 24 hours. Upon completion of the reaction detected by HPLC, the reaction mixture was filtered to recover Pd/C and concentrated to give a crude product. The crude product was purified with a column (mobile phase: 3% MeOH/DCM) to give a product (3.0 g, yield: 82%).

5. Synthesis of Y-Type Small Molecule 4

THF (20 mL) and triphenylphosphine (1.5 g) were added to the reaction product of the previous step (2 g). After the mixture was reacted overnight at room temperature, water (0.1 mL) was added and the reaction was continued overnight. The THF was evaporated to dryness, water (50 mL) was added, the resulting mixture was washed twice with toluene (40 mL), then twice with DCM (30 mL), the water was evaporated to dryness to give a product (1.5 g, yield: 86%).

NMR (D$_2$O) δ: 3.5-3.8 (m, 33H), 2.8 (m, 4H); ESI-MS: 443.4 (M+H).

Example 5: Synthesis of (HOOC-EG$_4$)$_2$-NH$_2$ (5)

Figure 5:
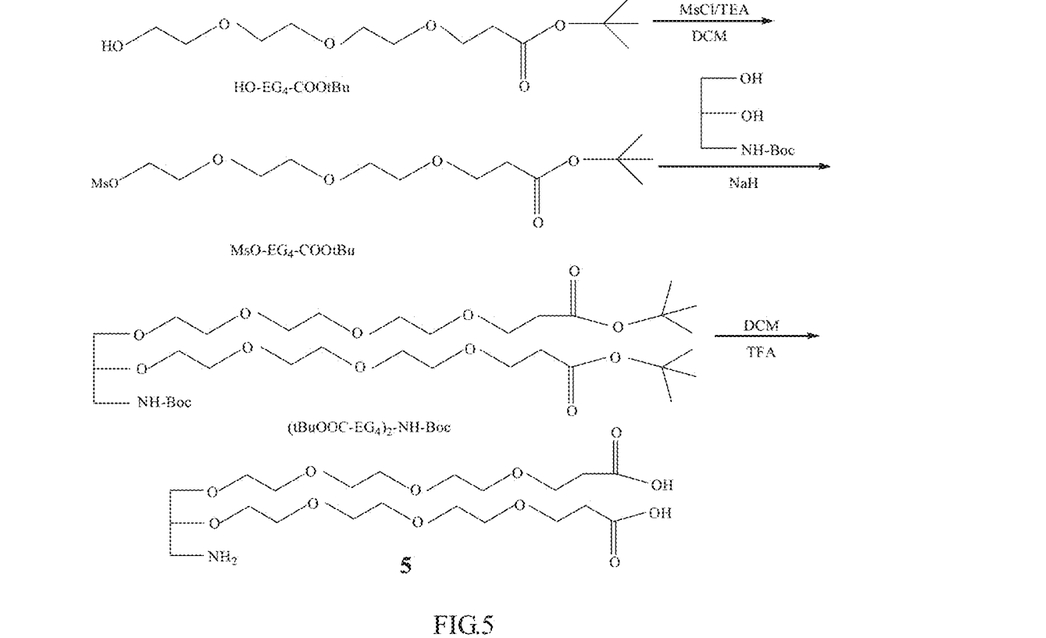
FIG. 5 is a synthetic route diagram of the Y-type discrete polyethylene glycol derivative $(HOOC-EG_4)_2$-$NH_2$ (5).

The synthetic route is shown in FIG. 5.

1. Synthesis of MsO-EG$_4$-COOtBu

DCM (350 mL) and TEA (22.7 mL) were added to HO-EG$_4$-COOtBu (39.4 g). A solution of MsCl (11.4 mL) in DCM (150 mL) was added under ice-water bath. The reaction was performed overnight at room temperature. The reaction mixture was washed 3 times with water (200 mL), dried over anhydrous sodium sulfate, filtered, and the solvent was removed by evaporation to give a product (45.5 g, yield: 93%).

2. Synthesis of (tBuOOC-EG$_4$)$_2$-NH-Boc

Toluene (75 mL) was added to 3-Boc-NH—1,2-propanediol (2 g), NaH (60%, 0.92 g) was added under an ice-water bath. The reaction was performed at room temperature for 2 hours. A toluene solution (80 mL) containing MsO-EG$_4$-COOtBu (9.2 g) was added dropwise, and the reaction was continued overnight at 60° C. The reaction mixture was detected by HPLC, the toluene was evaporated to dryness, the resulting mixture was washed once each with DCM and water, the DCM was evaporated to dryness to give a crude product. The crude product was purified with a column (mobile phase: 1-2% MeOH/DCM) to give a product (6.4 g, yield: 75%).

3. Synthesis of Y-Type Small Molecule 5

To the (tBuO-EG$_4$)$_2$-NH-Boc (2.3 g) prepared in Step 2 above, DCM (20 mL) and trifluoroacetic acid (TFA) (8 mL) were added, the reaction was performed overnight at room temperature. The solvent was evaporated to dryness, the resulting mixture was added with water, washed twice with EA, and the aqueous phase was evaporated to give a product (1.5 g, yield: 92.0%).

NMR (CDC$_3$) δ: 3.5-3.8 (m, 39H), 2.78 (n, 2H), 2.4 (t, 4H); ESI-MS: 588.4 (M+H)$^+$, 600.3 (M+Na)$^+$.

Example 6: Synthesis of (mEG$_3$)$_2$-EG$_4$-OH (6)

Figure 6:
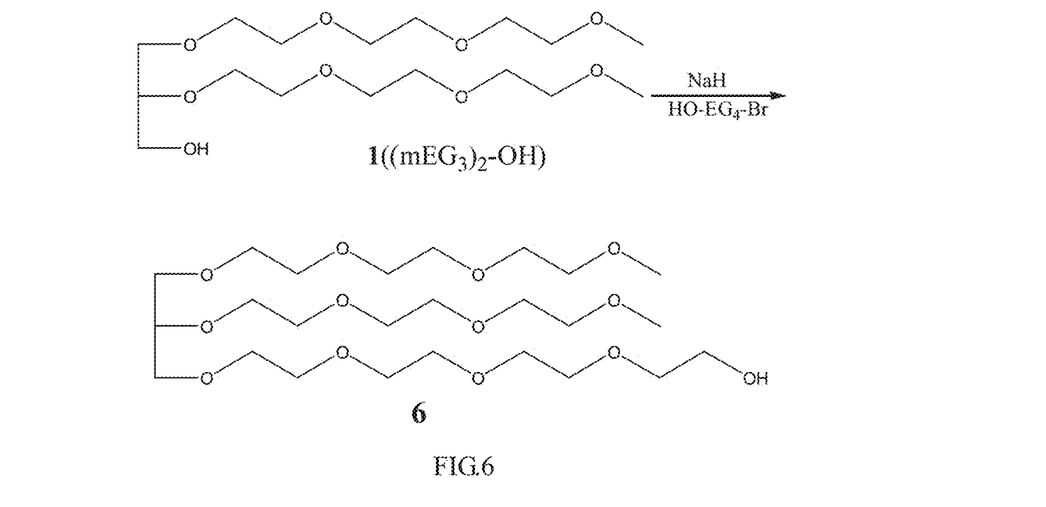
FIG. 6 is a synthetic route diagram of the Y-type discrete polyethylene glycol derivative $(mEG_3)_2$-$EG_4$-OH (6).

The synthetic route is shown in FIG. 6.

Toluene (50 mL) was added to (mEG$_3$)$_2$-OH (1) (2 g), the mixture was azeotroped to remove water. The toluene (about 20 mL) was distilled off. NaH (60%, 220 mg) was added under ice-water bath and stirred at room temperature for 2 hours. A solution of HO-EG$_4$-Br (1.47 g) in toluene (10 mL) was added dropwise. After the addition was complete, the mixture was heated to 60° C. and reacted overnight. Toluene is evaporated to dryness to give a crude product. The crude product was purified with a column (4% MeOH/DCM) to give a product (2.1 g, yield: 72.0%).

NMR (CDCl$_3$) δ: 3.5-3.8 (m, 45H), 3.37 (s, 6H); ESI-MS: 561.4 (M+H)$^+$, 583.4 (M+Na)$^+$.

Example 7: Synthesis of Three Derivatives of (mEG$_3$)-OH (1)

THF (20 mL) and pyridine (1.26 mL) were added to (1) (2 g) prepared in Example 1, and then cholesteryl chloroformate (2.46 g) was dissolved in THF (30 mL) and added dropwise to the reaction flask. The mixture was stirred at room temperature overnight. The completeness of the reaction was checked by TLC. The reaction mixture was washed once with water, spin-dried to give a crude product, and purified by column (2% MeOH/DCM) to give a cholesterol derivative (2.8 g, yield: 67.4%).

NMR (CDCl$_3$) δ: 5.45-5.55 (m, 1H), 4.50-4.65 (m, 1H), 4.0-4.1 (m, 2H), 3.5-3.8 (m, 27H), 3.38 (s, 6H), 0.80-2.50 (m, 40H), 0.60-0.65 (m, 3H).

DCM (20 mL) and pyridine (0.32 mL) were added to (1) (0.5 g) prepared in Example 1, and then hexadecyl chloroformate (0.86 mL) was dissolved in DCM (10 mL) and added dropwise to the reaction flask. The mixture was stirred at room temperature overnight. The completeness of the reaction was checked by TLC. The reaction mixture was washed with water, spin-dried to give crude product, and purified by column (2% MeOH/DCM) to give a hexadecanol derivative (0.65 g, yield: 76.6%).

NMR (CDCl$_3$) δ: 4.0-4.3 (m, 4H), 3.5-3.8 (m, 27H), 3.38 (s, 6H), 1.65 (m, 2H), 1.2-1.3 (m, 26H), 0.88 (t, 3H).

DCM (20 mL) and pyridine (0.32 mL) were added to (1) (0.5 g) prepared in Example 1, and then menthol chloroformate (0.41 mL) was dissolved in DCM (10 mL) and added dropwise to the reaction flask. The mixture was stirred at room temperature overnight. The completeness of the reaction was checked by TLC. The reaction mixture was washed with water, spin-dried to give crude product, and purified by column (2% MeOH/DCM) to give a menthol derivative (0.58 g, yield: 78.6%).

NMR (CDCl$_3$) δ: 4.4-4.6 (m, 1H), 4.1-4.3 (m, 2H), 3.5-3.8 (m, 27H), 3.38 (s, 6H), 1.9-2.1 (m, 2H), 1.0-1.7 (m, 7H), 0.7-0.9 (m, 9H).

Example 8: Synthesis of Three Derivatives of mEG$_7$-OH

Commercially available mEG$_7$-OH was used for preparation of three derivatives of mEG$_7$-OH under the same conditions as in Example 7.

Cholesterol derivative: NMR (CDCl$_3$) δ: 5.45-5.55 (m, 1H), 4.50-4.65 (m, 1H), 4.0-4.1 (m, 2H), 3.5-3.8 (m, 26H), 3.37 (s, 3H), 0.80-2.50 (m, 40H), 0.60-0.65 (m, 3H).

Hexadecanol derivative: NMR (CDCl$_3$) δ: 4.27 (t, 2H), 4.12 (t, 2H), 3.5-3.8 (m, 26H), 3.38 (s, 3H), 1.65 (m, 2H), 1.25 (m, 26H), 0.88 (t, 3H).

Menthol derivative: NMR (CDCl$_3$) δ: 4.4-4.6 (m, 1H), 4.2-4.3 (m, 2H), 3.5-3.8 (m, 26H), 3.38 (s, 3H), 1.9-2.1 (m, 2H), 1.0-1.7 (m, 7H), 0.7-0.9 (m, 9H).

Figure 7:
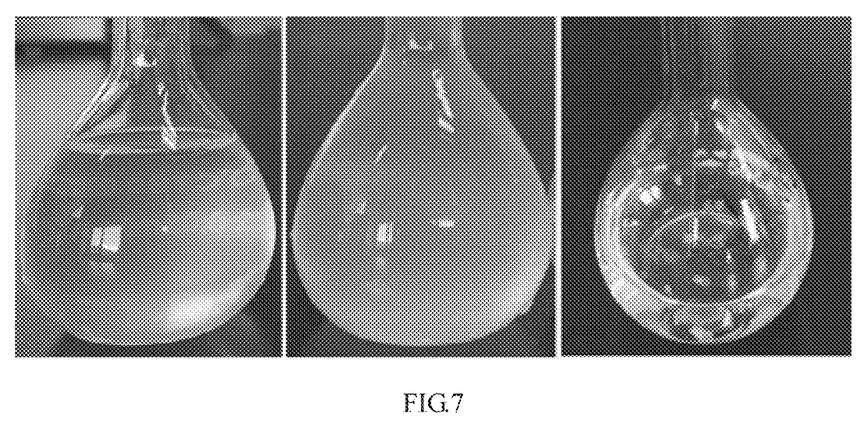
FIG. 7 shows the results of a comparison test for dispersibility of cholesterol and cholesterol derivatives in aqueous solution (from the left to the right are the aqueous solutions of cholesterol derivative of 1, cholesterol derivative of $mEG_7$-OH and cholesterol with the same concentration, respectively.)

Example 9: Comparison Test of Dispersibility of Cholesterol and Cholesterol Derivatives in Water 20 mg the cholesterol derivative of (1) prepared in Example 7, 20 mg the cholesterol derivative of mEG$_7$-OH prepared in Example 8 and 20 mg cholesterol were respectively placed in a 50 mL volumetric flask, which was then added with water to the scale, and placed in 20° C. water bath, shaken vigorously for 30 s every 5 min. The disperse state of the two cholesterol derivatives and cholesterol in water are shown in FIG. 7, from the left to the right are cholesterol derivative of (1), cholesterol derivative of mEG$_7$-OH and cholesterol, respectively. As shown in FIG. 7, the dispersion liquid of cholesterol derivative of (mEG$_3$)$_2$-OH is semitransparent and the handwriting behind the volumetric flask can be clearly seen; the cholesterol derivative of mEG$_7$-OH is a white emulsion, and cholesterol is completely insoluble.

Example 10: Comparison Test of Solubility of Cholesterol Derivatives in Water 20.0 mg cholesterol derivative of (1) prepared in Example 7 was dispersed in 50 mL water, 5 mL was taken out therefrom and added with 1.5 mL water, the resulting mixture was placed in a 20° C. water bath, and shaken vigorously for 30 s every 5 min. After 30 min, the solution was turbid; another 1.5 mL water was added, the resulting mixture was vigorously shaken for 30 s every 5 min until 14 mL water was added, and the solution became clear.

24.2 mg cholesterol derivative of mEG$_7$-OH prepared in Example 8 was dispersed in 50 mL of water, 5 mL was taken out therefrom and added with 5 mL water, the resulting mixture was shaken vigorously for 30 s every 5 min. After 30 mmin, the solution was turbid; another 5 mL water was added, the resulting mixture was vigorously shaken for 30 s every 5 min until 25 mL water was added. 5 mL solution was taken from the dilute solution, the same procedure was carried out until 10 mL water was added, and the solution became clear.

The results are shown in Table 1. From the analysis of the results, the cholesterol derivative of (1) has a solubility of 10.5 mg/100 g H$_2$O, which is 3.90 times the solubility of the cholesterol derivative of mEG$_7$-OH (2.69 mg/100 g H$_2$O), and 52.5 times the solubility of cholesterol (<0.2 mg/100 g H$_2$O).

Example 11: Comparison Test of Solubility of Hexadecanol Derivative in Water 111.0 mg the hexadecanol derivative of (1) prepared in Example 7 was dispersed in 25 μL of water and shaken vigorously for 30 s every 5 min. After 30 min, the solution was clear; another 50 μL water was added, the resulting mixture was vigorously shaken for 30 s every 5 min until 1.025 mL of water was added, and the solution remained clear.

112.9 mg the hexadecanol derivative of mEG$_7$-OH prepared in Example 8 was dispersed in 50 μL of water and shaken vigorously for 30 s every 5 min. After 30 min, the solution was turbid; another 50 μL water was added, the resulting mixture was vigorously shaken for 30 s every 5 min until 250 μL was added, and the solution became clear.

The results are shown in Table 1. From the analysis of the results, the hexadecanol derivative of (1) can be miscible with water in any proportion at room temperature, while the hexadecanol derivative of mEG$_7$-OH has a solubility of 45.2 g/100 g H$_2$O and hexadecanol has a solubility of <1 mg/100 g H$_2$O.

Example 12: Comparison Test of Solubility of Menthol Derivative in Water 106.7 mg the menthol derivative of (1) prepared in Example 7 was dispersed in 25 μL of water and shaken vigorously for 30 s every 5 min. After 30 min, the solution was clear; another 50 μL water was added, the resulting mixture was vigorously shaken for 30 s every 5 min until 1.025 mL water was added, and the solution remained clear.

101.3 mg the menthol derivative of mEG$_7$-OH prepared in Example 8 was dispersed in 50 μL of water and vigorously shaken for 30 s every 5 min. After 30 min, the solution was turbid; another 50 μL of water was added, the resulting mixture was vigorously shaken for 30 s every 5 min. After 30 min, the solution became clear.

The results are shown in Table 1. The menthol derivative of (1) can be miscible with water in any proportion at room temperature, while the menthol derivative of mEG$_7$-OH has a solubility of 67.5 g/100 g of H$_2$O and menthol has a solubility of <100 mg/100 g H$_2$O.

TABLE 1

| | The solubility of three derivatives | | |
|---|---|---|---|
| Modifier | Cholesterol | Hexadecanol | Menthol |
| — | <0.2 mg/100 g $H_2O$ | <1 mg/100 g $H_2O$ | <100 mg/100 g $H_2O$ |
| $mEG_7$-OH | 2.69 mg/100 g $H_2O$ | 45.2 g/100 g $H_2O$ | 67.5 g/100 g $H_2O$ |
| Y-type small molecule 1 | 10.5 mg/100 g $H_2O$ | miscible with water in any proportion | miscible with water in any proportion |

According to the above experimental results, taking cholesterol, hexadecanol and menthol as poorly soluble drug models, the modification with the discrete polyethylene glycol can greatly increase their solubility in water, and under the same conditions, the modification with Y-type discrete polyethylene glycol gives a higher degree of water solubility improvement than the linear discrete polyethylene glycol.

The invention claimed is:

1. A Y-type discrete polyethylene glycol derivative having the structure of formula (IV), (V), (VI), (VII), (IX):

wherein:
$E_1$ is a discrete polyethylene glycol group with a structure of $(CH_2CH_2O)_j$, j is an integer from 1 to 20;
$E_2$ is a discrete polyethylene glycol group with a structure of $(CH_2CH_2O)_k$, k is an integer from 1 to 20;
$E_3$ is a discrete polyethylene glycol group with a structure of $(CH_2CH_2O)_l$, l is an integer from 0 to 204-04; and
r, s and t are 0.

2. The Y-type discrete polyethylene glycol derivative of claim 1, wherein j is an integer from 1 to 12; and/or, k is an integer from 1 to 12; and/or, l is an integer from 1 to 12.

3. The Y-type discrete polyethylene glycol derivative of claim 1, wherein j is 1, 2, 3, 4, 5, 6, 7 or 8; and/or, k is 1, 2, 3, 4, 5, 6, 7 or 8; and/or, l is 1, 2, 3, 4, 5, 6, 7 or 8.

4. A The Y-type discrete polyethylene glycol derivative is $(N_3\text{-}EG_4)_2$-OH with a structure of:

or,
the Y-type discrete polyethylene glycol derivative is $(tBuOOC\text{-}EG_4)_2$-NH-Boc with a structure of:

5. A preparation method of the Y-type discrete polyethylene glycol derivative of claim 1, including: (1) halogenating or sulfonating one or more end-group-modified discrete polyethylene glycol derivatives; (2) reacting any of the products obtained in step (1) with at least one hydroxyl group of a core compound; and, (3) optionally, modifying the end group(s) of the product of step (2) to give a Y-type discrete polyethylene glycol derivative having the structure of formula (I), or, modifying the end group(s) of the product of step (2) into a hydroxyl group, then reacting with any of the products obtained in step (1), modifying the end group(s) of the obtained product to give a Y-type discrete polyethylene glycol derivative having the structure of formula (I);
the end-group-modified discrete polyethylene glycol derivative in step (1) has a structure of Z—X—$(CH_2)_n$-E-OH,
wherein:
X is a linking group selected from the group consisting of —$(CH_2)_i$—, —$(CH_2)_i$NH—, —$(CH_2)_i$OCOO—, —$(CH_2)_i$OCONH—, —$(CH_2)_i$NHCONH—, —OC$(CH_2)_i$COO—, —$(CH_2)_i$COO— and —$(CH_2)_i$CONH—, i is an integer from 0 to 10;
Z is selected from the group consisting of the active end groups defined by Y in the structure of formula (I), or, Z is selected from the group consisting of methyl ester group, ethyl ester group, tert-butyl ester group, aldehyde acetal group, benzyloxy, tert-butoxy, imidogen, halogen and hydroxy;
the Y is: hydrogen, $C_1$-$C_6$ alkyl, $C_1$-$C_6$ alkoxy, hydroxy, amino, aminomethyl, maleimido, carboxyl, sulfydryl, succinimide carbonate, succinimide acetate, succinimide propionate, succinimide succinate, succinimide, dithiopyridinyl, propionic acid group, aldehyde group, thioester group, acryloxy, azido, glutaric acid group, hydrazide, alkynyl, p-nitrophenyl carbonate, isocyanato, o-dithiopyridinyl, silane, carboxymethyl, vinyl sulfone group or vitamin H;
E is a discrete polyethylene glycol group with a structure of $(CH_2CH_2O)_a$, a is an integer from 0 to 100;
the core compound in step (2) has a structure of formula (X):

wherein:

r, s, and t are independently selected from 0, 1, 2, 3;

$R_1$, $R_2$ and $R_3$ are selected from the group consisting of hydroxy, allyloxy, benzyloxy, tert-butoxy, azido, imino, ester, halogen, methoxy, ethoxy, amino, sulfydryl, carboxyl, aldehyde group, acryloxy, maleimide, vinyl sulfone group and vitamin H, and at least one of $R_1$, $R_2$ and $R_3$ is hydroxy.

6. The preparation method of claim 5, wherein the Z is methyl ester group, ethyl ester group, tert-butyl ester group, azido, aldehyde acetal group or benzyloxy.

7. The preparation method of claim 5, wherein in the core compound (X), two of $R_1$, $R_2$ and $R_3$ in the core compound are hydroxy.

8. The preparation method of claim 5, wherein the reaction for sulfonating the end-group-modified discrete polyethylene glycol derivative in the step (1) is as follows:

wherein, the G is methyl or p-tolyl.

9. The preparation method of claim 5, wherein the reaction in the step (2) of the preparation method is as follows:

wherein, W is —OMs, —OTs, —Cl, —Br, or —I;

$Z_1$ and $Z_2$ are independently selected from the group consisting of the reactive end groups defined by the Z; and $E_1$ and $E_2$ are independently selected from the group consisting of discrete polyethylene glycol groups defined by the E.

10. The preparation method of claim 5, wherein the step (1) is: adding methylene chloride in a volume ratio of 1 to 100 times and triethylamine in a molar ratio of 1 to 5 times to one end-group-modified discrete polyethylene glycol derivative, then dissolving methane chloride or p-toluenesulfonyl chloride in a molar ratio of 1-3 times in methylene chloride in a volume ratio of 1 to 30 times and adding dropwise into a reaction flask, reacting at room temperature for 1 to 48 hours, washing the reaction solution with water 1-3 times, drying the organic phase with anhydrous sodium sulfate, filtering to remove the sodium sulfate, evaporating the solvent to dryness and concentrating to give a product, i.e., the sulfonylated product of the end-group-modified discrete polyglycol derivative.

11. The preparation method of claim 5, wherein the step (2) is: adding toluene in a volume ratio of 1 to 50 times to the core compound, adding 60% sodium hydride with a mass-to-volume ratio of 0.5-1.0 g/mL under an ice-water bath, reacting for 1 to 3 hours at room temperature, adding dropwise the product of step (1) in a mass ratio of 5-10 times to sodium hydride, and toluene in a volume ratio of 1 to 50 times reacting at 60-70° C. for 1 to 48 hours, evaporating the toluene to dryness, adding dichloromethane and water, each washing once, evaporating the dichloromethane to dryness, and column-purifying with mobile phase being 1-3% methanol/dichloromethane to give a product.

* * * * *